(12) United States Patent
Parthasaradhi Reddy et al.

(10) Patent No.: US 10,336,706 B2
(45) Date of Patent: Jul. 2, 2019

(54) CRYSTALLINE FORM OF ELTROMBOPAG FREE ACID

(71) Applicant: HETERO RESEARCH FOUNDATION, Hyderabad (IN)

(72) Inventors: Bandi Parthasaradhi Reddy, Hyderabad (IN); Kura Rathnakar Reddy, Hyderabad (IN); Jonnala Sambi Reddy, Hyderabad (IN); Bandi Vamsi Krishna, Hyderabad (IN)

(73) Assignee: HETERO RESEARCH FOUNDATION, Balanagar Hyderabad (IN)

( * ) Notice: Subject to any disclaimer, the term of this patent is extended or adjusted under 35 U.S.C. 154(b) by 0 days.

(21) Appl. No.: 15/508,540

(22) PCT Filed: Sep. 2, 2015

(86) PCT No.: PCT/IB2015/056655
§ 371 (c)(1),
(2) Date: Mar. 3, 2017

(87) PCT Pub. No.: WO2016/035018
PCT Pub. Date: Mar. 10, 2016

(65) Prior Publication Data
US 2017/0275255 A1 Sep. 28, 2017

(30) Foreign Application Priority Data

Sep. 5, 2014 (IN) .............................. 4374/CHE/2014

(51) Int. Cl.
*C07D 231/46* (2006.01)
*C07C 201/12* (2006.01)
*C07D 231/08* (2006.01)

(52) U.S. Cl.
CPC .......... *C07D 231/46* (2013.01); *C07C 201/12* (2013.01); *C07D 231/08* (2013.01)

(58) Field of Classification Search
CPC .................................................. C07D 231/46
See application file for complete search history.

(56) References Cited

U.S. PATENT DOCUMENTS

2010/0256212 A1* 10/2010 Leksic ................. C07D 231/46
514/404

FOREIGN PATENT DOCUMENTS

| CN | 103819406 | 4/2015 | |
| IN | 1946/MUM/2014 | * 6/2014 | |
| WO | 2001089457 | 11/2001 | |
| WO | 2003098992 | 12/2003 | |
| WO | 2013072921 | 5/2013 | |
| WO | 2014177517 | 11/2014 | |
| WO | 2015111085 | 7/2015 | |
| WO | WO 2015111085 A2 * | 7/2015 | ........... C07C 201/08 |
| WO | 2015139536 | 9/2015 | |
| WO | 2017081014 | 5/2017 | |

OTHER PUBLICATIONS

"Reflux." Merriam-Webster.com. Merriam-Webster, n.d. Web. Sep. 25, 2017.*
P. Revill, Eltrombopag Antithrombocytopenic Thrombopoietin Receptor Agonist, Drugs of the Future (2006), 31 (9):767-770, Prous Science, Barcelona, Spain.
Disclosed Anonymously, Salts and Polymorphs of (z)-3'-(2-(1-(3,4-Dimethylphenyl)-3-Methyl-5-Oxo-1H-Pyrazol-4(5H)-Ylidene)Hydrazinyl)-2'-Hydroxybiphenyl-3-Carboxylic Acid, IPCOM000190390D, Nov. 26, 2009, IP.com, Prior Art Database.
Disclosed Anonymously, Salts and Polymorphs of (z)-3'-(2-(1-(3,4-Dimethylphenyl)-3-Methyl-5-Oxo-1H-Pyrazol-4(5H)-Ylidene)Hydrazinyl)-2'-Hydroxybiphenyl-3-Carboxylic Acid, IPCOM000204540D, Mar. 2, 2011, IP.com, Prior Art Database.

* cited by examiner

*Primary Examiner* — Matthew P Coughlin
(74) *Attorney, Agent, or Firm* — Cantor Colburn LLP

(57) ABSTRACT

The present invention relates to crystalline form of Eltrombopag free acid and its process for preparation.

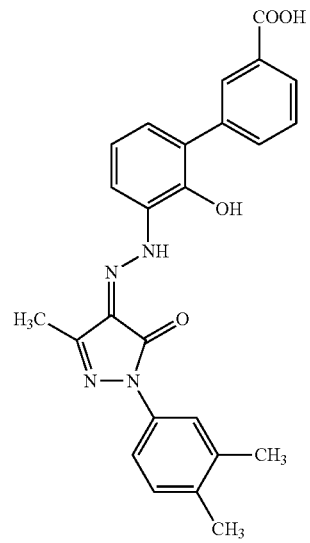

2 Claims, 3 Drawing Sheets

CRYSTALLINE FORM OF ELTROMBOPAG FREE ACID

CROSS-REFERENCE TO RELATED APPLICATIONS

This application is a 371 of PCT/IB15/56655, filed on Sep. 2, 2015, which claims the benefit of Indian Provisional Patent Application No. 4374/CHE/2014, filed on Sep. 5, 2014, the under provisions of 35 U.S.C. 119 and the International Convention for the protection of Industrial Property.

FIELD OF THE INVENTION

The present invention relates to the crystalline form of Eltrombopag free acid and its process for preparation.

BACKGROUND OF THE INVENTION

Eltrombopag chemically known as (Z)-3'-(2-(1-(3, 4-dimethylphenyl)-3-methyl-5-oxo-1H-pyrazol-4(5H)-ylidene) hydrazinyl)-2'-hydroxybiphenyl-3-carboxylic acid having the following chemical compound of formula I:

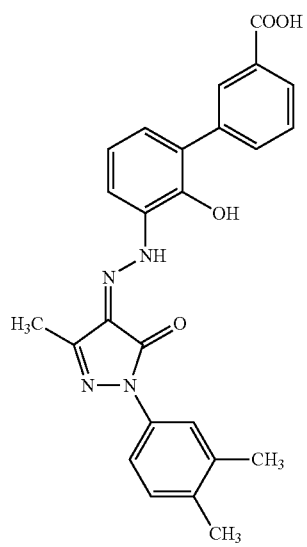 [SMILES: CC1=NN(c2ccc(C)c(C)c2)C(=O)/C1=N\Nc1cccc(-c2cccc(C(=O)O)c2)c1O]

Eltrombopag is marketed as bis-(monoethanolmine) or Olamine salt under the trade name PROMACTA® by GlaxoSmithKline, which is shown as formula II:

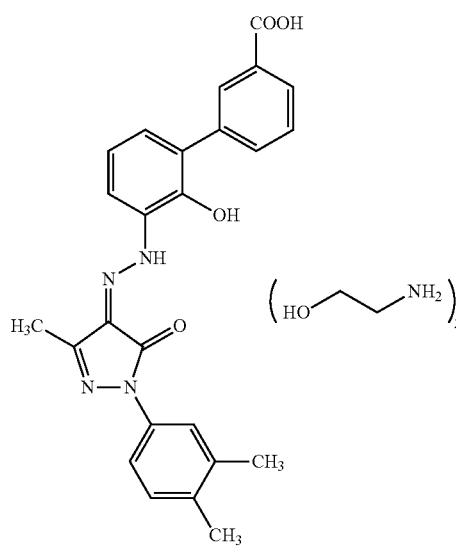

Eltrombopag bis-(monoethanolmine) is useful as an agonist of thrombopoietin (TPO) mimetic receptor, particularly in the treatment of thrombocytopenia. Eltrombopag interacts with the transmembrane domain of the TPO receptor (also known as cMp1) leading to increased platelet production.

U.S. Pat. No. 7,160,870 (the U.S. '870 patent) discloses Eltrombopag and its salts. U.S. Pat. No. 7,547,719 discloses, bisethanolamine salt of Eltrombopag, which is also known as olamine salt of Eltrombopag. U.S. '870 to patent discloses a process for the preparation of Eltrombopag free acid, which is shown schematically by Scheme I:

Scheme I

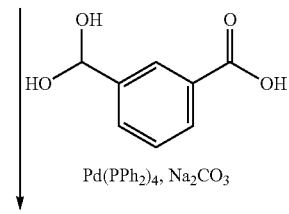

Pd(PPh$_2$)$_4$, Na$_2$CO$_3$

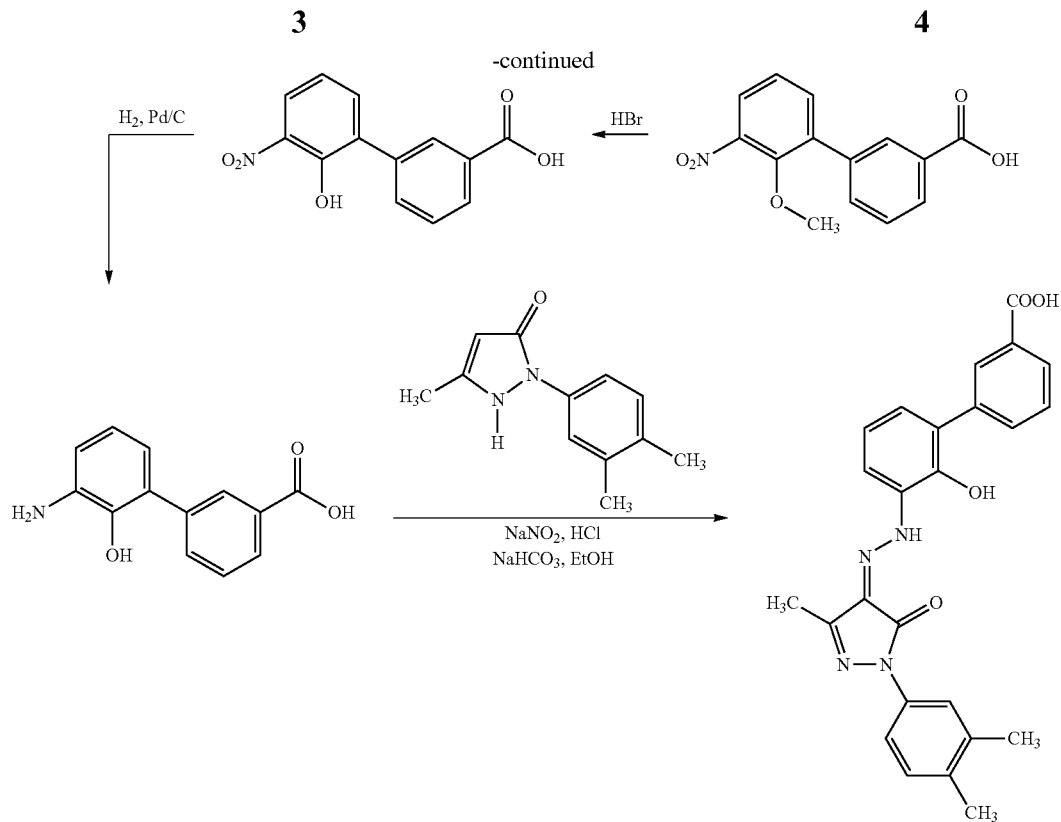

U.S. Pat. No. 7,956,048 B2 discloses different crystalline forms of Eltrombopag free acid as well as process for the preparation of crystalline forms. U.S. '048 patent also discloses characterization of crystalline forms (PXRD & $^{13}$C NMR). Different process for the preparation of crystalline forms and their characterization has been described below:

| Crystalline form and its Process | 2θ (±0.2) | 13C NMR (±0.2 ppm) |
|---|---|---|
| Anhydrous Form I: A mixture of Eltrombopag Form I and Form III (500 mg) was suspended in acetone (30 mL) and heated to 57° C. Water (10 mL) was added and the resulting suspension was left to cool to reach a temperature of 22° C. The precipitate was filtered and dried for 1 h at 50° C./5 mbar to yield 314 mg. Or Eltrombopag Form III (96 mg) was dissolved in 10 mL of glacial acetic acid (99.5%) while heating to boiling point of glacial acetic acid (118° C.). The hot solution was then filtered and left to crystallize while cooling to room temperature (23° C.). The obtained product was collected by filtration and dried at 35° C., under vacuum. 40 mg of bright orange product was obtained. Or A mixture of Eltrombopag Form I and Form III, (230 mg) was dissolved in 25 mL of glacial acetic acid (99.5%) while heating. The hot solution was then filtered and left to crystallize while cooling in an ice bath. The obtained product was collected by filtration and dried at 35° C. under vacuum. 139 mg of bright orange product was obtained. Or Eltrombopag Form III (24.42 g, HPLC purity: 98%) was suspended in 470 ml of glacial acetic acid (>99.5%) in a 1 L reactor. The suspension was stirred for five hours under reflux, then cooled to 40° C. and stirred for one hour at the same temperature. Crystals formed and were filtrated off, washed with 100 mL of methanol:water (1:1) and dried at 60° C./0 mbar for twelve hours yielding | 4.0, 7.3, 7.7, 12.1 and 16.1 | 166.9, 155.4, 141.4, 134.1, 130.4, 125.7, 119.8 and 117.8 |

-continued

| Crystalline form and its Process | 2θ (±0.2) | 13C NMR (±0.2 ppm) |
|---|---|---|
| 20.49 g orange solid of Eltrombopag form I (Yield = 88%; HPLC purity: 99.94%). Or Crude Eltrombopag (151 g, HPLC purity: 98.5%) was suspended in 2.9 L of glacial acetic acid in 3 L reactor. The suspension was stirred for five hours under reflux and cooled to 40° C. Crystals formed and were filtrated off, washed with 200 mL of methanol:water (1:1) and dried at 60° C./0 mbar overnight yielding 133 g orange solid of pure Eltrombopag free acid (HPLC: 99.8%; XRPD: Form I). | | |
| Form III: Eltrombopag (210 mg) was dissolved in 15 mL of ethyl acetate while heating at reflux (77° C.). The hot solution was then filtered and left to crystallize while cooling in an ice bath (0-5° C.). The obtained product was collected by filtration and dried overnight at 22° C. 82 mg of bright orange product was obtained. | 9.2, 11.2, 12.2 and 14.0 | 170.6, 128.7, 124.2 and 113.8 |
| Form IV: Eltrombopag (500 mg) Form I was suspended in Methanol/water mixture 1:3 (40 mL) and heated to 80° C. The suspension was left to cool to 22° C. The precipitate was filtered, washed with Methanol and air dried on air over night to yield 321 mg. | 8.4, 11.0, 13.1, 21.1 and 22.0 | — |
| Form V: A mixture of Eltrombopag Form I and Form III (500 mg) was dissolved in tetrahydrofuran (10 mL) and mixture of water/Methanol (1:1, 10 mL) was added dropwise. The precipitate was filtered and dried for 2 h at 50° C./5 mbar to yield 340 mg. Or A mixture of Eltrombopag Form I and Form III (500 mg) was dissolved in tetrahydrofuran (10 mL) and water (10 mL) was added dropwise. The solution was stirred 1 hour during which a precipitate was formed. The precipitate was filtered, washed with tetrahydrofuran/water (1:1, 10 mL) and dried for 2 h at 50° C./5 mbar to yield 423 mg. Or Eltrombopag Form VIII (1.092 g) was dissolved in 6.4 mL of tetrahydrofuran while heating at 60° C. When a clear solution was obtained, 6.4 ml of water was added and reaction mixture was stirred for 1 hour at 22° C. A solid precipitated and was filtered, washed with water, and dried at 50° C. under vacuum, 1 hour. 1.023 g of bright orange product was obtained. Or Eltrombopag (8.65 g) was dissolved in tetrahydrofuran (50 mL) with heating to reflux. Water (50 mL) was added dropwise and the solution was stirred for 1 hour at 22° C. during which a precipitate was formed. The precipitate was filtered, washed with water and dried for 2 h at 50° C./5 mbar to yield 7.70 g. | 5.3, 9.2, 14.0 | 171.9, 155.4, 136.3, 121.3 |
| Form VI: Eltrombopag Form V (2 mg) was placed in aluminum sample pan with a small hole on lid under nitrogen pouring at a flow rate of 35 ml/min. The sample was equilibrated at 20° C., heated with heating rate of 10° C. per minute up to 120° C. | 5.9, 8.4, 8.8, 10.3, 11.7, 14.7, 16.2, 23.5 and 24.8 | — |
| Form VII: Eltrombopag Form V (2 mg) was placed in aluminum sample pan with a small hole on lid under nitrogen pouring at a flow rate of 35 ml/min. The sample was equilibrated at 20° C., heated with heating rate of 10° C. per minute up to 213° C. The DSC was calibrated with indium. The sample was cooled at a rate of 10° C./min up to 20° C. | 7.3, 12.5, 18.8, 22.5 and 26.0 | — |
| Form VIII: Eltrombopag Form IV (500 mg) was suspended in dichloromethane (10 mL) and water (5 mL). The suspension was basified with sodium hydroxide, 1M (2.5 mL) and then acidified with hydrochloric acid, | 5.3, 11.0, 17.0, 19.1 and 28.2 | — |

| Crystalline form and its Process | 2θ (±0.2) | 13C NMR (±0.2 ppm) |
|---|---|---|
| 1M (2.5 mL). The solid was filtered off and dried in a vacuum oven for 1/2 h on 50° C./5 mbar | | |
| Form IX: Eltrombopag Form I (15-20 mg) was dissolved in tetrahydrofuran (2 mL) with heating and left at 22° C. | 8.8, 10.9, 13.4 and 26.7 | — |
| Form X: Eltrombopag Form I (15-20 mg) was dissolved in dimethylsulfoxide (2 mL) with heating and left at 22° C. | 8.2, 13.2, 16.3 and 25.3 | — |
| Form XI: Eltrombopag Form I (15-20 mg) was dissolved in acetone (6 mL) with heating, filtered and left at 22° C. | 4.1, 8.1, 12.1 and 16.2 | — |
| Form XII: Eltrombopag form I (15-20 mg) was dissolved in methoxybenzene (anisole) (6 mL) with heating. Solution was left at 22° C. | 4.6, 7.6, 8.9, 10.4, 13.3, 14.1, 15.1, 16.2 and 23.9 | — |
| Form XIII Eltrombopag Form I (15-20 mg) was dissolved in diethyl ether (6 mL), with heating, filtered and left at 22° C. | 3.9, 7.8, 11.7, 12.4, 15.5, 20.5, 23.0 and 25.0 | — |
| Form XIV: Eltrombopag Form I (15-20 mg) was dissolved in ethyl acetate (6 Ml) with heating, filtered and left at 22° C. Obtained crystals were analyzed by powder XRD. | 4.0, 5.0, 7.9, 9.1, 10.7, 15.1, 19.0 and 21.4 | — |
| Form XV: Eltrombopag Form X (2 mg) was placed in a DSC and was heated to a temperature of 160° C., under $N_2$ | 4.0, 8.1, 9.4, 11.5 12.0, 16.2, 12.5, 20.9 and 27.8 | — |
| Form XVI: Crystalline 3'-amino-2'-hydroxybiphenyl-3-carboxylic acid Form II (50 g, 218 mmol, PXRD pattern at FIG. 34) (Supplier: Topharman Shangai Co., Ltd; Batch No: BPCA: 090921BPCA) was added to a solvent mixture of methanol (1 L) and hydrochloric acid; 4M (137 mL) in a 1 L reactor with stirring at room temperature (cca 22° C.). The resulting solution was stirred for 1A h and then cooled to 0-5° C. A refrigerated solution of sodium nitrite (15 g, 217 mmol) in water (50 mL) was added to the reaction mixture over 20 min (maintaining the reaction temperature below 10° C.) and the stirring was continued for 1 h. A Solution of sulfamic acid (2.22 g, 23 mmol) in water (50 mL) was added to the reaction mixture and stirred for 1 h at 5° C. The resulting reaction mixture was heated to room temperature and triethylamine (cca 80 mL) was added to adjust to pH 7-8. Crystalline 1-(3,4-dimethylphenyl)-3-methyl-1H-pyrazol-5-ol ("pyrazole") form II (44 g, 218 mmol, PXRD pattern at FIG. 33) (Supplier: Topharman Shangai Co., Ltd; Batch No: 090805PYRAZOL) was added in one portion to the reaction mixture and stirred for 2 h at room temperature, maintaining the pH 7-8. Hydrochloric acid (4M, cca 40 mL) was added to adjust the pH to 8 over 20 minutes with stirring. The precipitated solid was filtered, washed and dried at 40° C./5 bar for about 18 h to yield 100 g (90%) of EBP as a bright orange powder | 5.9, 7.1, 9.5, 11.2, 13.9, 15.4, 17.4, 21.2, 25.5 and 26.2 | 168.7, 156.7, 127.6, 112.8 |

U.S. Pat. No. 7,956,048 B2 also discloses Eltrombopag olamine crystalline forms, its process for preparation and designated as Form I, Form II and Form III. Further, this patent also discloses Eltrombopag olamine amorphous form and its process for preparation.

However, prior-art Eltrombopag free acid crystalline forms reported above are not pure crystalline form and contain some amount of amorphous form, and hence not stable. The present inventors have found that the acetic acid used during the preparation leads to unpure crystalline forms, which are not stable. In view of this present inventors have avoided acetic acid and found a crystalline form of Eltrombopag free acid, which is stable, reproducible and free of other polymorphic forms.

OBJECTIVES

The objective of the present invention is Eltrombopag free acid in crystalline form free of other polymorphic forms.

Another objective of the present invention, a process for the preparation of Eltrombopag free acid in pure crystalline form.

Another object of the present invention, a process for the preparation of Eltrombopag olamine salt by using crystalline form of Eltrombopag free acid.

SUMMARY OF THE INVENTION

The present invention relates to Eltrombopag free acid crystalline form, which is designated herein as Form H1.

In another embodiment, the present invention relates to a process for the preparation of crystalline Eltrombopag Form H1, which comprises:
 a) treating Eltrombopag in a solvent;
 b) heating the mixture of step (a);
 c) cooling the reaction mass of step (b); and
 d) isolating crystalline Eltrombopag Form H1.

In another embodiment the present invention relates to use of crystalline Eltrombopag Form H1 in the preparation of crystalline Eltrombopag olamine salt Form I.

DETAILED DESCRIPTION OF THE INVENTION

The present invention relates to Eltrombopag pure crystalline form, designated as Form H1.

According to one aspect of the present invention, crystalline Eltrombopag Form H1 is characterized by Powder X-Ray Diffraction, having peaks at about 6.3, 7.0, 9.0, 11.5, 12.7, 14.2, 20.5, 23.1, 25.5 and 28.6±0.2 degrees.

In another aspect of the present invention, crystalline Eltrombopag Form H1 is prepared by a process comprises, treating Eltrombopag in a solvent, selected from the group comprising of polar aprotic solvents, alcoholic solvents or mixture thereof; heating to reflux temperature at 50-100° C., preferably 70-90° C.; cooling the solution to below 35° C., preferably 25-30° C. to and isolating the obtained compound.

In another aspect of the present invention, polar aprotic solvent is selected from the group comprising of tetrahydrofuran, ethyl acetate, acetone, dimethyl sulfoxide, dimethyl formamide, acetonitrile; Alcoholic solvents is selected from the group comprising of methanol, ethanol, n-butanol, isopropanol; preferably dimethyl formamide, methanol.

In another aspect of the present invention, crystalline Eltrombopag Form H1 is isolated using conventional techniques such as centrifugation and filtration.

In another aspect of the present invention, crystalline Eltrombopag Form H1 is used in the preparation of crystalline Eltrombopag Olamine salt Form I.

In another aspect of the present invention, the process for preparing crystalline Eltrombopag olamine salt Form I, comprises:
 a) dissolving crystalline Eltrombopag Form H1 in tetrahydrofuran;
 b) optionally treatment with Carbon;
 c) addition of 2-amino alcohol (Olamine) solution (prepared by dissolving Olamine in ethanol);
 d) removal of the solvent; and
 e) isolating crystalline Eltrombopag Olamine salt Form I.

In another aspect of the present invention, the removal of the solvent is carried out in rotavapor, by evaporation, distillation etc., In another aspect of the present invention, industrially applicable crystallization processes were followed by using polar aprotic solvents instead of acetic acid to avoid the contamination of other crystalline forms.

In another aspect of the present invention, Eltrombopag is obtained by following the processes known in the prior-art.

POWDER X-RAY DIFFRACTION METHOD

Figure 1:
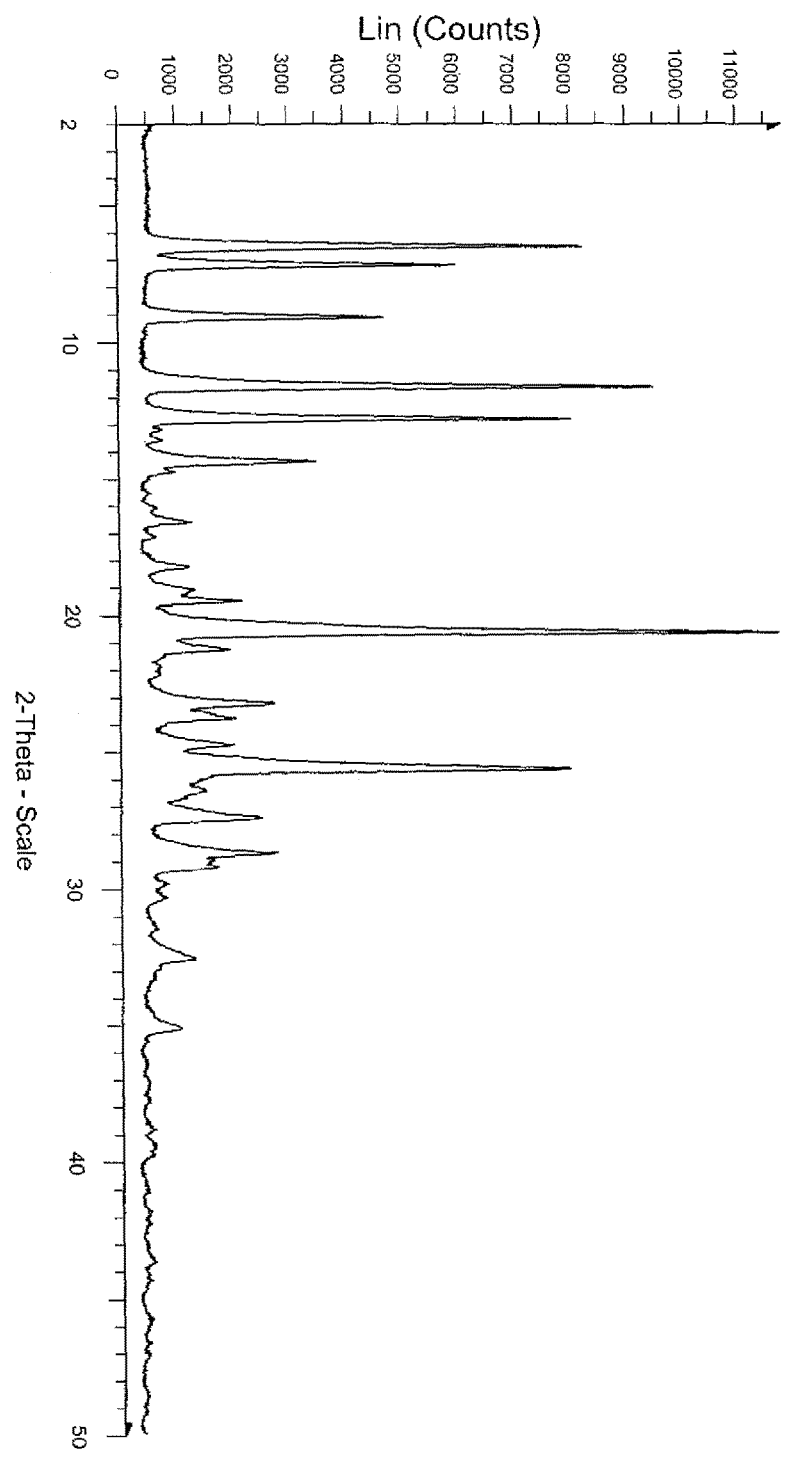
FIG. 1 is a X-ray powder diffraction spectrum of crystalline Eltrombopag Form H1 obtained as per Example 1.

X-ray powder diffraction spectrum was measured on a broker axs D8 advance X-ray powder diffractometer having a copper-Kα radiation. Approximately 1 gm of sample was gently flattered on a sample holder and scanned from 2 to 50 degrees two-theta, at 0.02 degrees two theta per step and a step time of 10.8 seconds. The sample was simply placed on the sample holder. The sample was rotated at 30 rpm at a voltage 40 KV and current 35 mA.

In the following section embodiments are described by way of examples to illustrate the process of invention. However, these do not limit the scope of the present invention. Variants of these examples would be evident to persons ordinarily skilled in the art.

Comparative Example: Preparation of Crystalline Eltrombopag Form I a. Preparation of 5-bromo-2-nitrophenol 3-Bromophenol (32.9 g, 0.19 mol) was added slowly to a cold (10° C.) solution of sodium nitrate (29.0 g, 0.34 mol) in conc. sulfuric acid; (40.0 g) and water (70.0 mL) and the resulting mixture was allowed to stir at room to temperature for 2 h. Water (200 mL) was added and the resulting mixture was extracted with diethyl ether and the extract was dried (MgSO4), filtered and concentrated. The residue was purified by flash chromatography (silica gel, 10% ethyl acetate/hexanes) to afford first the title compound (8.1 g, 20%), Mp 40-42° C., then the undesired isomer, 3-bromo-4-nitrophenol, as a yellow solid (12.7 g, 31%). Mp=125-127° C.

b. Preparation of 3'-Hydroxy-4'-nitrobiphenyl-4-carboxylic acid

A solution of the compound from comparative Example a (2.18 g, 0.01 mol.), 4-carboxyphenylboronic acid; (1.74 g, 0.0105 mol.), 2M aqueous sodium carbonate (10.0 mL; 0.02 mol.) and tetrakistriphenylphosphino palladium (0.5 g) in 1,4-dioxane (60.0 mL) was stirred and heated under reflux under a nitrogen atmosphere for 24 h, The reaction mixture was cooled and evaporated and the residue treated with 6M aqueous hydrochloric acid; (100 mL). The grey precipitate was filtered and washed well with water then diethyl ether to afford the title compound (2.3 g; 88%) as a colorless solid.

c. Preparation of 4'-Amino-3'-hydroxybiphenyl-4-carboxylic acid Hydrochloride Salt A solution of the compound from comparative Example b (1.6 g, 0.0062 mol.) in ethanol (75.0 mL), water (50.0 mL) and 3M aqueous sodium hydroxide (2.0 mL, 0.0062 mol.)

was hydrogenated over 10% palladium on carbon (0.2 g) at room temperature and 50 psi for 2 h.

The reaction mixture was filtered, treated with 3M aqueous hydrochloric acid; (25.0 mL) then evaporated and the residue triturated with little water to afford the title compound (1.18 g; 72%) as a brown solid.

d. Preparation of 1-(3,4-Dimethylphenyl)-3-methyl-3-pyrazolin-5-one

A solution of 3,4-dimethylphenylhydrazine hydrochloride (17.7 g; 0.1 mol.), ethyl acetoacetate (13.0 g; 0.1 mol.) and sodium acetate (8.2 g; 0.1 mol.) in glacial acetic acid; (250 mL) was stirred and heated under reflux for 24 h. The mixture was cooled and evaporated and the residue dissolved in diethyl ether (1 L) and carefully washed with saturated aqueous sodium hydrogen carbonate (5×200 mL). The ethereal layer was evaporated to afford the title compound (15.4 g; 76%).

e. Preparation of Eltrombopag

A suspension of the compound from comparative Example c (1.0 g; 0.0044 mol.) in 1M aqueous hydrochloric acid; (15.0 mL) was cooled to 5° C. then treated dropwise with a solution of sodium nitrite (0.32 g; 0.0046 mol.) in water (5.0 mL). The yellow mixture was stirred at 5° C. for a further 10 min. then treated in one portion with the compound from comparative Example d (0.882 g, 0.0044 mol.) followed by the portion-wise addition of sodium hydrogen carbonate (1.8 g; 0.022 mol.) and ethanol (20.0 mL) ensuring the final pH of the reaction mixture is approximately 7-8. The red solution was then stirred at room temperature for 24 h.

The mixture was filtered to give a red solid which was slurried in water (50.0 mL) and then acidified with concentrated hydrochloric acid. Filtration afforded the title compound (0.68 g; 35%) as an orange powder, Mp=280° C.

f. Preparation of Crystalline Eltrombopag Form I

Crude Eltrombopag (50 g) was suspended in 800 ml of glacial acetic acid in reactor. The suspension was stirred for five hours under reflux and cooled to 40° C. Crystals formed were filtrated off, washed with 200 ml of methanol:water (1:1) and dried at 60° C. yielding 40 gm orange solid of crystalline Eltrombopag Form I.

EXAMPLES

Example 1

Preparation of Crystalline Eltrombopag Form H1

Eltrombopag (15 g) was added to dimethylformamide (300 ml) in a reactor. The contents were heated to reflux at 75° C. for 75 minutes and then slowly cooled to 35° C. To the obtained solution, methanol was added and heated to reflux for 75 minutes and the contents were cooled slowly to obtain a solid mass. The obtained product mass was filtered and dried to yield crystalline Eltrombopag Form H1.

Yield: 13 g
Chromatographic Purity: 99.66% (by HPLC)
PXRD: As shown in FIG. 1.

Example 2

Preparation of Crystalline Eltrombopag Form H1

Eltrombopag (13.5 Kg) was added to dimethylformamide (165 L) in a reactor. The contents were heated to reflux at 75° C. for 75 minutes and then slowly cooled to 35° C. To the obtained solution, methanol (220 L) was added and heated to reflux for 75 minutes and the contents were cooled slowly and then washed with methanol (60 L). The obtained product mass was filtered and dried to yield crystalline Eltrombopag Form H1.

Figure 2:
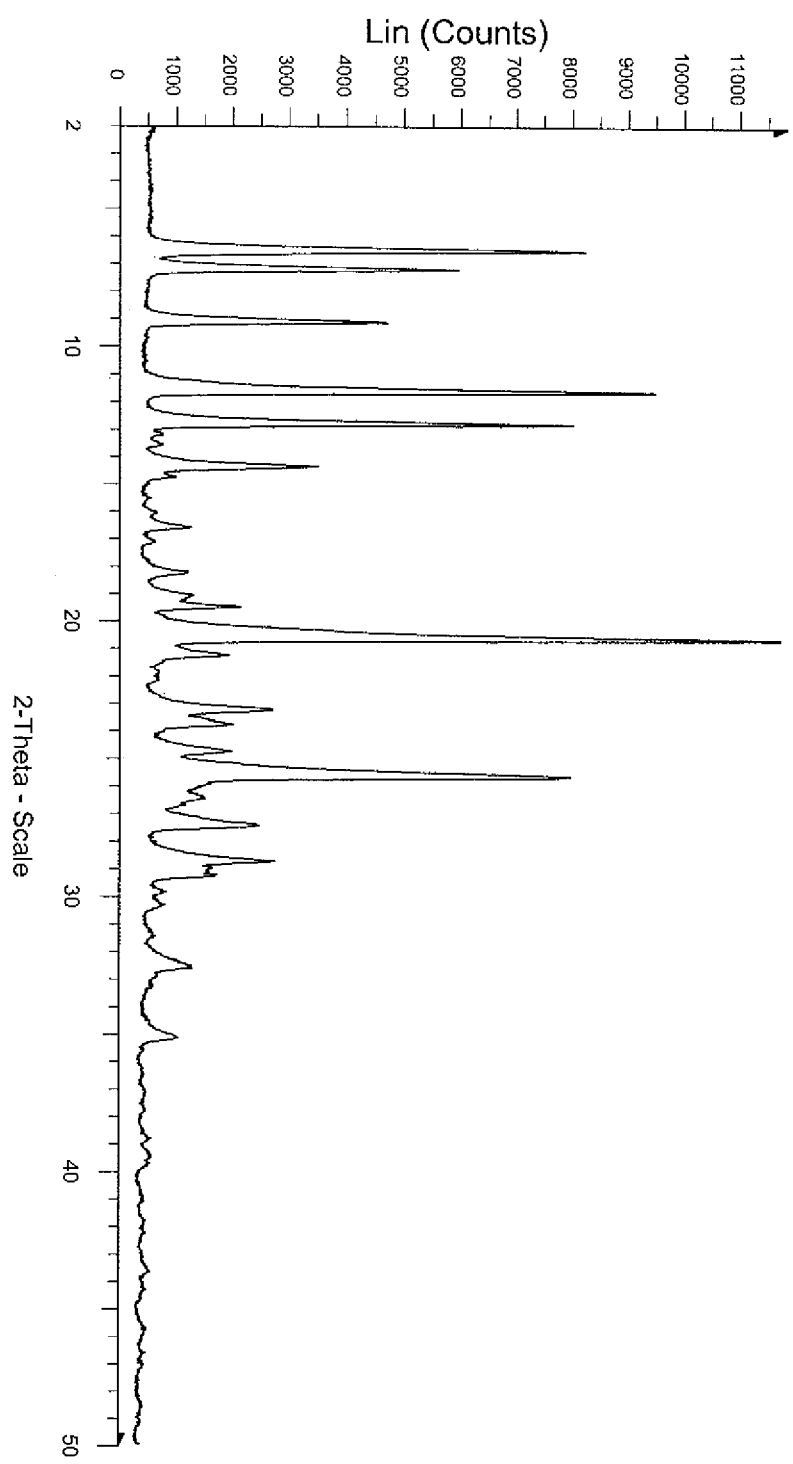
FIG. 2 is a X-ray powder diffraction spectrum of crystalline Eltrombopag Form H1 obtained as per Example 2.

Yield: 12 Kg
Chromatographic Purity: 99.76% (by HPLC)
PXRD: As shown in FIG. 2.

Example 3

Preparation of Crystalline Eltrombopag Olamine Salt Form I

Crystalline Eltrombopag Form H1 (15 Kg) was added to tetrahydrofuran (135 L) in a reactor. 2-amino alcohol dissolved in ethanol (165 L) was added to the above solution and stirred. After completion of the reaction, the solvent was distilled partially, thereafter cooled to 31° C. and stirred for 5 hrs. The obtained product was filtered, washed with ethanol and dried to yield Eltrombopag olamine salt Form I.

Figure 3:
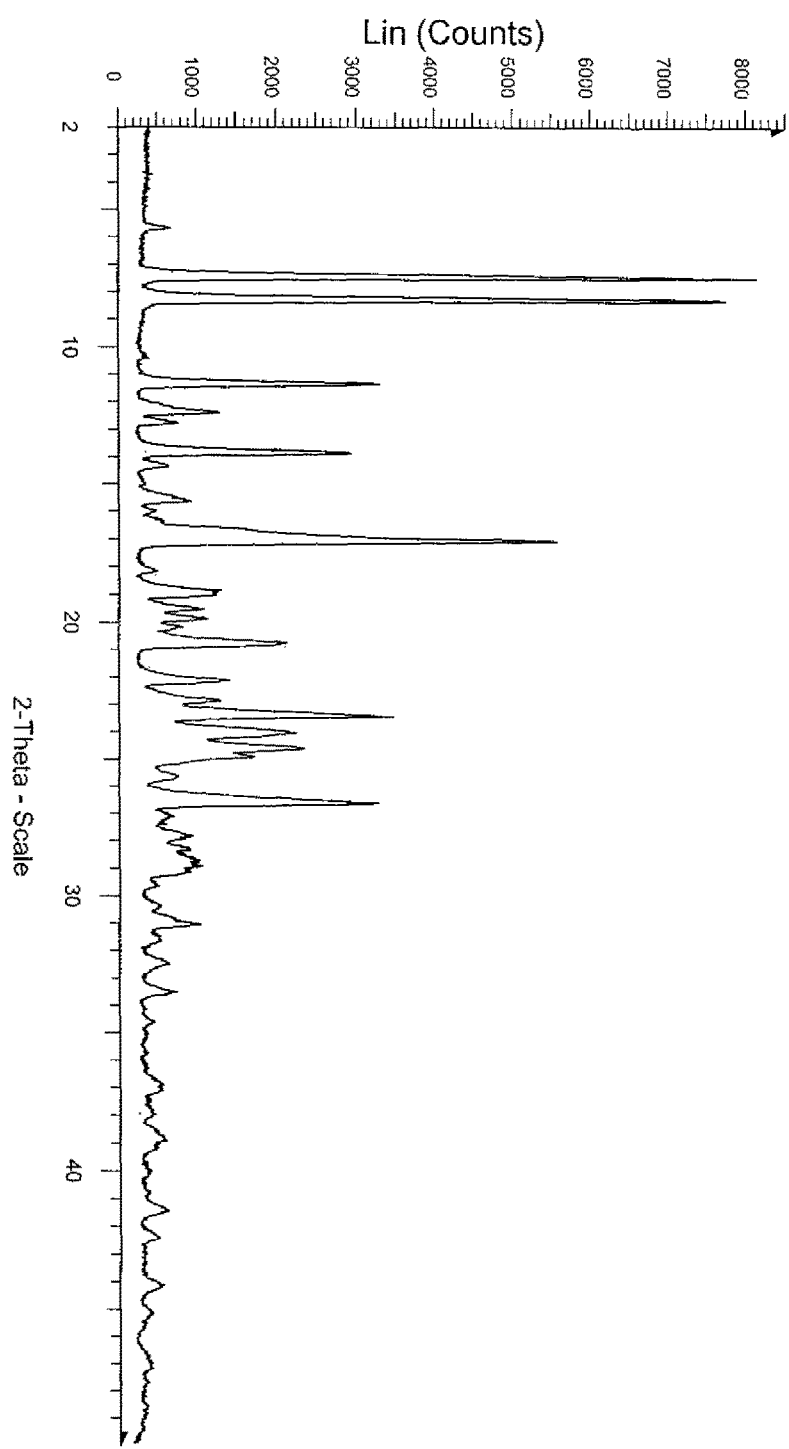
FIG. 3 is a X-ray powder diffraction spectrum of crystalline Eltrombopag Olamine salt Form I obtained as per Example 3.

Yield: 13 Kg
Chromatographic Purity: 99.2% (by HPLC)
PXRD: As shown in FIG. 3.

We claim:

1. A process for the preparation of crystalline Eltrombopag Form H1 having 2θ angle positions at about 6.3, 7.0, 9.0, 11.5, 12.7, 14.2, 20.5, 23.1, 25.5 and 28.6±0.2 degrees, which comprises:
   a) dissolving Eltrombopag in dimethyl formamide;
   b) heating the solution to reflux at 50-100° C.;
   c) cooling the solution to below 35° C. and adding an alcoholic solvent selected from methanol, ethanol, n-butanol, and isopropanol;
   d) heating the solution to reflux at 50-100° C. and e) isolating the crystalline Eltrombopag Form H1.

2. A process for the preparation of crystalline Form 1 of Eltrombopag Olamine, which comprises:
   a) preparing crystalline Eltrombopag Form H1 according to the method of claim 1 and dissolving said crystalline Eltrombopag Form H1 in tetrahydrofuran;
   b) optionally treating with Carbon;
   c) adding an alcoholic solution of 2-amino alcohol and ethanol;
   d) removing the solvents; and
   e) isolating crystalline Eltrombopag Olamine salt Form I.

* * * * *